(12) United States Patent
Meester

(10) Patent No.: US 11,439,296 B2
(45) Date of Patent: Sep. 13, 2022

(54) METHOD AND APPARATUS USING A MEDICAL IMAGING HEAD FOR FLUORESCENT IMAGING

(71) Applicant: Quest Photonic Devices B.V., Middenmeer (NL)

(72) Inventor: Richard Johannes Cornelis Meester, Wieringerwerf (NL)

(73) Assignee: Quest Photonic Devices B.V., Middenmeer (NL)

( * ) Notice: Subject to any disclaimer, the term of this patent is extended or adjusted under 35 U.S.C. 154(b) by 557 days.

(21) Appl. No.: 16/491,578

(22) PCT Filed: Mar. 9, 2018

(86) PCT No.: PCT/NL2018/050147
§ 371 (c)(1),
(2) Date: Sep. 6, 2019

(87) PCT Pub. No.: WO2018/164579
PCT Pub. Date: Sep. 13, 2018

(65) Prior Publication Data
US 2021/0137369 A1 May 13, 2021

(30) Foreign Application Priority Data

Mar. 9, 2017 (NL) ...................... 2018494

(51) Int. Cl.
*A61B 1/04* (2006.01)
*A61B 1/06* (2006.01)
(Continued)

(52) U.S. Cl.
CPC ............ *A61B 1/043* (2013.01); *A61B 1/0638* (2013.01); *A61B 1/0646* (2013.01);
(Continued)

(58) Field of Classification Search
CPC ..... A61B 1/043; A61B 1/0638; A61B 5/0035; A61B 5/0071
See application file for complete search history.

(56) References Cited

U.S. PATENT DOCUMENTS 4,562,831 A * 1/1986 Murakoshi ............... A61B 1/05
348/E5.029
4,651,201 A * 3/1987 Schoolman ............ G02B 30/35
348/45

(Continued)

FOREIGN PATENT DOCUMENTS

JP 3962122 11/1996
JP H10-201707 8/1998
(Continued)

*Primary Examiner* — Anh Tuan T Nguyen
*Assistant Examiner* — Jae Woo
(74) *Attorney, Agent, or Firm* — N.V. Nederlandsch Octrooibureau

(57) ABSTRACT

The invention relates to a method for detecting visible and infrared light using a medical imaging system, said medical imaging system comprising a camera module configured to receive a visible light signal and at least one infrared light signal from an object image. The medical imaging system for detecting visible and comprises
an input for visible light for illuminating a tissue;
an input for excitation light for exciting a fluorescence agent in the tissue;
a camera module configured to receive a visible light signal and at least one infrared light signal from an object image in the tissue. The camera module comprises at least a first, second, and third optical path for directing light from the object image to a first, second, and third filter and sensor combination respectively. In any order, the first, second, and third filters are a green filter, an infrared filter, and a red/blue patterned filter comprising red and blue filters in alternating pattern.

(Continued)

Half of the red/blue patterned filter is a red filter and the other half is a blue filter. The green and infrared light are thus sampled at full sensor resolution, for the red and blue light spatial interpolation is required.

18 Claims, 10 Drawing Sheets

(51) Int. Cl.
    *A61B 5/00*         (2006.01)
    *G02B 5/20*         (2006.01)
    *G02B 27/10*       (2006.01)
    *G02B 27/12*       (2006.01)

(52) U.S. Cl.
    CPC .......... *A61B 5/0035* (2013.01); *A61B 5/0071* (2013.01); *A61B 5/0086* (2013.01); *G02B 5/208* (2013.01); *G02B 27/1013* (2013.01); *G02B 27/126* (2013.01); *A61B 1/042* (2013.01)

(56) References Cited

U.S. PATENT DOCUMENTS

| | | | | |
|---|---|---|---|---|
| 4,938,205 | A * | 7/1990 | Nudelman | A61B 1/0008 257/E31.115 |
| 5,419,313 | A * | 5/1995 | Lemke | A61B 1/00165 600/133 |
| 5,459,605 | A * | 10/1995 | Kempf | A61B 1/00193 359/476 |
| 5,751,341 | A * | 5/1998 | Chaleki | A61B 1/00096 348/E13.058 |
| 5,895,350 | A * | 4/1999 | Hori | A61B 1/0607 600/109 |
| 6,293,911 | B1 * | 9/2001 | Imaizumi | A61B 1/00009 600/178 |
| 6,465,968 | B1 * | 10/2002 | Sendai | A61B 5/0071 600/160 |
| 6,561,973 | B1 * | 5/2003 | Bala | A61B 1/042 600/168 |
| 8,602,971 | B2 * | 12/2013 | Farr | A61B 1/227 600/173 |
| 2002/0013513 | A1 * | 1/2002 | Bala | A61B 1/042 600/178 |
| 2002/0035330 | A1 * | 3/2002 | Cline | A61B 1/00009 600/478 |
| 2002/0103439 | A1 * | 8/2002 | Zeng | G01J 3/0289 600/476 |
| 2003/0007087 | A1 | 1/2003 | Hakamata et al. | |
| 2003/0233024 | A1 * | 12/2003 | Ando | A61B 1/00096 600/111 |
| 2004/0186351 | A1 | 9/2004 | Imaizumi et al. | |
| 2005/0027166 | A1 * | 2/2005 | Matsumoto | A61B 1/00186 977/852 |
| 2007/0041720 | A1 * | 2/2007 | Iketani | A61B 1/0646 396/17 |
| 2008/0027286 | A1 * | 1/2008 | Xie | A61B 1/00096 600/181 |
| 2008/0207996 | A1 * | 8/2008 | Tsai | G02B 23/2407 600/112 |
| 2009/0076329 | A1 * | 3/2009 | Su | A61B 1/0008 600/166 |
| 2011/0063427 | A1 * | 3/2011 | Fengler | H04N 5/332 348/E5.09 |
| 2011/0292258 | A1 * | 12/2011 | Adler | G02B 23/2423 348/263 |
| 2012/0206582 | A1 * | 8/2012 | DiCarlo | A61B 1/04 348/222.1 |
| 2012/0268573 | A1 * | 10/2012 | Schonborn | A61B 5/418 348/E13.074 |
| 2013/0300837 | A1 * | 11/2013 | DiCarlo | A61B 1/00193 348/46 |
| 2016/0022126 | A1 * | 1/2016 | Ramesh | A61B 1/045 600/109 |
| 2016/0100763 | A1 | 4/2016 | Fengler et al. | |
| 2017/0020377 | A1 | 1/2017 | Takeuchi et al. | |
| 2017/0215711 | A1 * | 8/2017 | Kobayashi | H04N 5/2258 |
| 2017/0237960 | A1 * | 8/2017 | Kamm | H04N 9/04557 348/46 |
| 2017/0289467 | A1 * | 10/2017 | Yamamoto | H04N 9/04553 |
| 2017/0293134 | A1 * | 10/2017 | Otterstrom | A61B 1/0638 |
| 2017/0360287 | A1 * | 12/2017 | Morimoto | A61B 1/05 |
| 2018/0168455 | A1 * | 6/2018 | Tesar | C03C 17/3452 |
| 2019/0306479 | A1 | 10/2019 | Takenaga et al. | |
| 2021/0235980 | A1 * | 8/2021 | Oosake | A61B 1/0638 |

FOREIGN PATENT DOCUMENTS

| | | |
|---|---|---|
| JP | 2002-16931 | 1/2002 |
| JP | 2016-178995 | 10/2016 |

\* cited by examiner

Fig. 3A

| R1 | R2 | B2 | B4 | R10 | R12 | B15 | B17 | R19 | R20 |
|----|----|----|----|-----|-----|-----|-----|-----|-----|
| R3 | R4 | B1 | B3 | R9  | R11 | B14 | B16 | R18 |     |
|    | R5 | R6 | R7 | R8  | B9  | B10 | B11 | B12 | R17 |
| B5 | B6 |    |    |     |     |     |     |     | R17 |
| B7 | B8 |    |    | R13 | R14 |     |     |     |     |
|    |    |    |    | R15 | R16 |     |     |     |     |

Fig. 3B

| G1 | G2 | G3 | G4 | G5 | G6 | G11 | G12 | G17 | G18 | G23 | G24 | G29 | G30 | G35 | G36 |
| G7 | G8 | G9 | G10 |   |    | G15 | G16 | G21 | G22 | G27 | G28 | G33 | G34 |
| G13| G14|    |    |   |    | G19 | G20 | G25 | G26 | G31 | G32 |

Fig. 3C

| I1 | I2 | I3 | I4 | I5 | I6 | I11 | I12 | I17 | I18 | I23 | I24 | I29 | I30 | I35 | I36 |
| I7 | I8 | I9 | I10|    |    | I15 | I16 | I21 | I22 | I27 | I28 | I33 | I34 |
| I13| I14|    |    |    |    | I19 | I20 | I25 | I26 | I31 | I32 |

Fig. 3D

| I1 | I2 | J1 | J2 | I5 | I6 | J9 | J10 | I11 | I12 | J13 | J14 | I17 | I18 | I19 | I20 |
| I3 | I4 | J3 | J4 | I7 | I8 | J11| J12 | I9  | I10 | J15 | J16 |
| I13| I14| J5 | J6 |    |    |    |     | I11 | I12 |
| I15| I16| J7 | J8 |

METHOD AND APPARATUS USING A MEDICAL IMAGING HEAD FOR FLUORESCENT IMAGING

FIELD OF THE INVENTION

The present invention relates to a method for detecting visible and infrared light using a medical imaging system and to said medical imaging system. The medical imaging system may be used in an open lens configuration or an endoscope or a laparoscope.

BACKGROUND ART

Various clinical applications using Infrared (IR) or Near-Infrared (NIR) light have been described in the literature. In such applications, a contrast agent may be used which is introduced into living tissue that is to be examined, and which is absorbs or emits IR light. In some applications, there are multiple wavelength ranges of IR light which are of interest.

When a device such as an endoscope is used in a clinical application using IR light, the professional using the endoscope typically also wants to use visible light camera sensing for eye-hand coordination when using the endoscope. The endoscope camera must thus sense red, green, and blue visible light and at least one (N) IR wavelength range. The camera must also generate the images at a high enough image frequency, or frame rate, to make reliable eye-hand coordination possible. A minimal frame rate is typically 60 frames per second.

This poses certain constraints on the camera. Current state of the art colour cameras are 3CCD image heads, which have a single incoming light entrance and then split the incoming light into three optical paths ending in three respective filter sensor combinations. Each sensor typically senses one primary colour, e.g. red, green, and blue. The three colours are typically projected through a prism at different CCDs but physically look to the same location (the origin of the incoming light). This way for each location the exact R, G and B pixel values are sensed. In order to also sense IR light, such a camera would need a fourth optical path which can be provided by adding a further prism or beam splitter. However, this increasing "stacking" of prisms and beam splitters has a problem in that in order to have all sensors in its focal plane, the first prism is physically the largest, decreasing when progressing, in order to compensate the total focal length and compensate all sensors.

For measuring visible light, it is also possible to use a single sensor (CCD) combined with a Bayer filter, for example having a 2×2 filter pattern of R-G/G-B patterns. Then for each pixel location, only one of the pixel values R, G, and B are sensed. The missing pixels need to be interpolated, which gives rice to an interpolation error especially in case of fine detail. Furthermore the red and blue pixels are one out of four pixels while green is two out of four of these Bayer filters due to the fact that red and blue provide less information to the human eye. Effectively, 50% of the pixels in the sensor's pixel grid "sees" green light, while only 25% of the pixels receives red light and another 25% of the pixels receives blue light. This specifically results in high interpolation errors in the red and blue signals due to pixel noise which can no longer be filtered out because of the low amount of neighbouring red or blue pixels. This means that hot or dead pixels are difficult to cancel and give significantly reduced image performance resulting in visible artefacts. In order to also measure IR light, either a fourth filter must be added (thus increasing the interpolation error) or a second optical path must be made (increasing the volume).

Both approaches have drawbacks and show that there is a balance between spatial errors due to interpolation and pixel noise when using filters and volume increase due to adding extra prisms (or other types of beam splitters) for additional optical paths when not using Bayer filters.

U.S. Pat. No. 8,620,410 discloses a medical imaging system that provides simultaneous rendering of visible light and fluorescent images. It uses two optical paths, one for visible light which is registered by a (single sensor) video camera and one for infrared which is registered by an infrared camera. A drawback of such a system is that the visible light camera, in order to generate a colour image using a single CCD sensor, a Bayer filter is used to split the incoming light once into red, green, and blue components. This reduces the resolution of the visible light image, which is disadvantageous, specifically in endoscopic or laparoscopic imaging systems.

U.S. Pat. No. 9,173,554 addresses that problem by using three optical paths, created by a dichroic prism assembly, which are respectively used for red, green and blue light sensing. In order to be able to measure a fourth component for infrared fluorescence radiation, the optical path leading to the red light sensor is used to detect both red and infrared light, in a time alternating fashion. The light source used in the application must also alternatingly emit red and infrared light, in sync with the sensor. In this manner, the spatial resolution is maintained (no spatial interpolation error). However, now there is a temporal interpolation effect, since the red and infrared lights are sampled at half the frame rate of the green and blue lights. The effectively reduced frame rate and consequently increased time lag hampers the eye-hand coordination of the person using the endoscope.

Furthermore when lower levels of red or infrared light are to be measured, a longer exposure time is required, which can also influence the real time behaviour of the colour image. This approach also does not allow for any calculations that require simultaneous multiple signals from red and infrared wavelengths. Also adding another IR channel reduces the framerate further since now it must be used to detect Red, IR1, IR2, which results in ⅓th of the max frame time, resulting in noticeable artefacts and thus is a clear limit of this technology.

Furthermore, the red and infrared images cannot both be exactly in focus. Due to a large wavelength difference between red and infrared, at best either the IR image is sharp and in focus or the R image is sharp and in focus. Due to the switching, the sensors can only be set at the same exposure time, because switching exposure time would require sensor settings that influence with the readout timing and exposure time, which can no longer overlap and ultimately influence either framerate and/or sensitivity of the system as well as adding a great deal of system processing complexity. Finally, gain needs to be switched heavily to differ between low signal-strength IR signals and relatively high signal-strength R signals. This negatively influences either the sensitivity of the IR channel and/or the red channel as well as frame time due to time it takes to apply the sensor settings before starting the exposure.

It is an object of the invention to provide a practical solution for detecting both visible light and IR light, which does not require time-switching of the received signals.

SUMMARY OF THE INVENTION

The invention provides a method for detecting visible and infrared light using a medical imaging system, said medical imaging system comprising a camera module configured to receive visible light and infrared light from an object image, the method comprising:
- exciting a fluorescence agent in a tissue sample with excitation light;
- illuminating the tissue sample with visible light;
- receiving light from the object image, said light comprising visible light and one or more infrared fluorescence light originating from the fluorescence agent;
- splitting the received light into a first, second, and third optical path;
- filtering the received light in the first, second, and third optical path through a first, second and third optical filter, respectively;
- detecting the filtered light in the first, second, and third optical path with a first, second and third sensor, respectively wherein the first, second, and third filters, in any order, are a green filter, an infrared filter, and a red/blue patterned filter comprising red and blue filters in alternating pattern so that half of the light received by the red/blue patterned filter goes through a blue filter and half of the light received by the red/blue patterned filter goes through a red filter.

The invention further provides a medical imaging system for detecting visible and infrared light, said medical imaging system comprising
- an input for visible light for illuminating a tissue;
- an input for excitation light for exciting a fluorescence agent in the tissue;
- a camera module configured to receive visible light and infrared light from an object image in the tissue, the camera module comprising at least a first, second, and third optical path for directing light from the object image to a first, second, and third sensor respectively, wherein:
  - the first optical path is provided with a first filter,
  - the second optical path is provided with a second filter, and
  - the third optical path is provided with a third filter, wherein the first, second, and third filters, in any order, are a green filter, an infrared filter, and a red/blue patterned filter comprising red and blue filters in alternating pattern so that half of the light received by the red/blue patterned filter goes through a blue filter and half of the light received by the red/blue patterned filter goes through a red filter.

According to the present invention, the tissue sample may be an in-vivo tissue sample or an ex-vivo tissue sample.

As mentioned, in the method and the system, half of the light received by the red/blue patterned filter goes through a blue filter and half of the light received by the red/blue patterned filter goes through a red filter. In effect, there is one sensor which receives 100% green light, one sensor which receives 100% infrared light, and one sensor which receives 50% red light and 50% blue light, in a manner which makes accurate interpolation of the missing red and blue pixels possible. All sensors may operate at the same frame rate, there is no need for temporal subsampling as in the cited prior art.

In an embodiment, the medical imaging system comprises a dichroic prism assembly configured to receive the light from the object image through an entrance face of the dichroic prism assembly, comprising at least a first, second, and third prism, each prism having a respective first, second, and third exit face, wherein:
- the first exit face is provided with the first sensor,
- the second exit face is provided with the second sensor, and
- the third exit face is provided with the third sensor.

The invention further provides an open lens system, an endoscope and a laparoscope comprising a medical imaging system, more particularly a dichroic prism assembly, as described above.

The invention further provides a medical imaging system comprising at least one dichroic prism assembly as described above, wherein at least two infrared imaging wavelength (e.g. between 640 and 1000 nm) sensors and three visible wavelength (e.g. red, green, and blue) sensors are used, wherein each of the sensors are optically pixel to pixel aligned with a accuracy of better than ⅕th of a pixel.

The imaging system may be used for real-time applications during surgery. In an embodiment, the frame rate is at least 50 frames per second (fps) and the pixels are sampled with at least 8 bits. For better eye-hand coordination, a frame rate of at least 60 frames per second or even at least 90 or 100 frames per second is preferred. The bit depth of the pixels may be the indicated 8 bits or more, e.g. 10, 12 or 16 bits.

BRIEF DESCRIPTION OF THE DRAWINGS

The present invention will be discussed in more detail below, with reference to the attached drawings, in which:

FIGS. 3a-d schematically show filters for use on sensors of a dichroic prism assembly according to an embodiment of the invention;

DESCRIPTION OF EMBODIMENTS

Figure 1A:
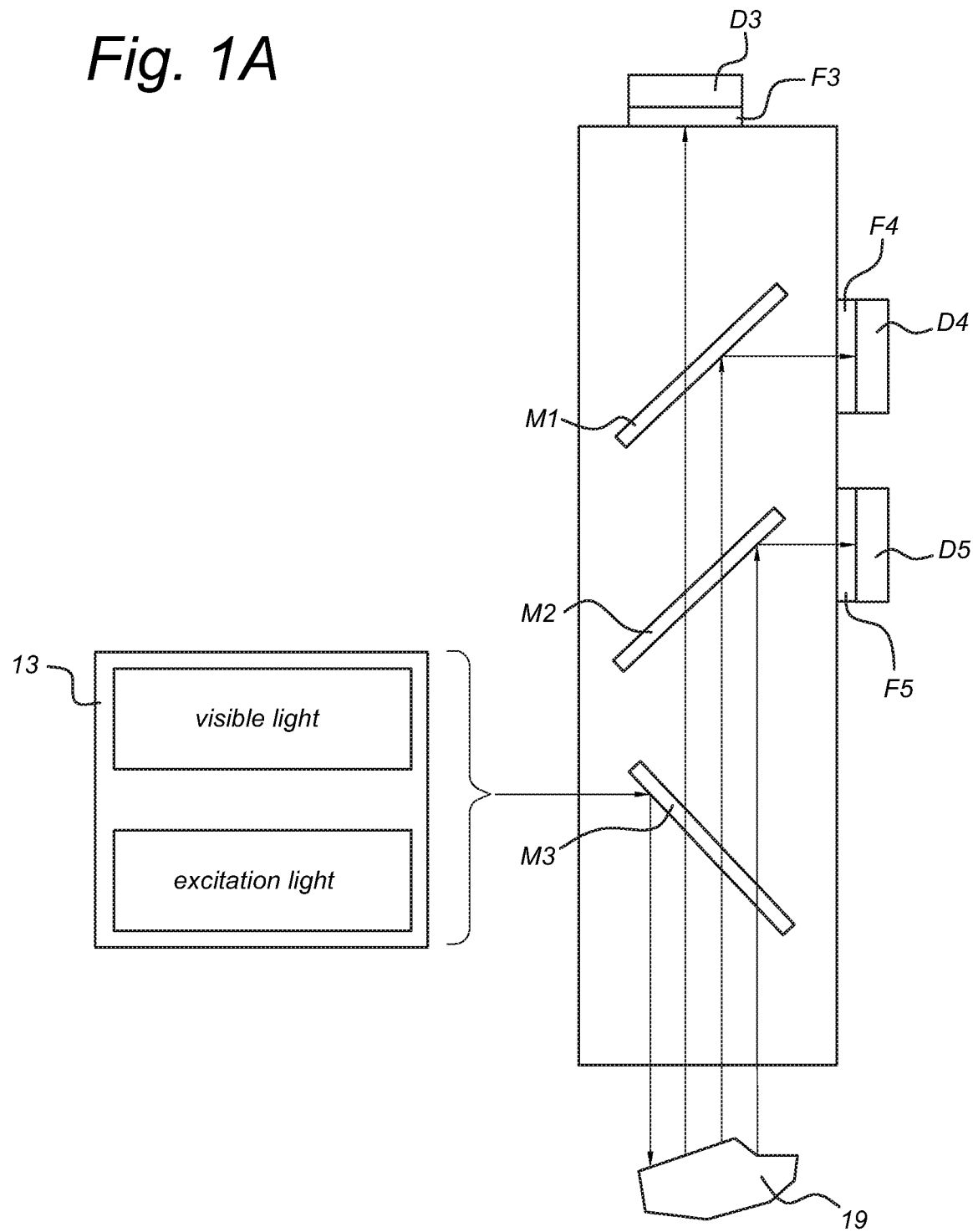
FIG. 1a schematically shows a medical imaging system according to a an embodiment of the invention.

FIG. 1a schematically shows a medical imaging system according to an embodiment of the invention. The figure shows four optical paths: one optical path for transmitting visible and excitation light from the visible and excitation light sources 13 to a tissue 19, and three optical paths for transmitting light (visible and fluorescence light) from the tissue 19 to the towards, respectively, light sensors D3, D4, and D5. Each respective light sensor D3, D4, D5 is provided with a filter F3, F4, and F5. The optical paths can be made using dichroic mirrors M1, M2, M3. For clarity, lenses and other optical instruments are omitted from FIG. 1a.

The filters F3, F4, and F5 will be discussed in reference to FIGS. 3a-d which schematically show filters for use on sensors of a dichroic prism assembly according to an embodiment of the invention. It is understood that the optical path for transmitting visible and excitation light does not need to coincide with the any of the other optical paths and that the visible and excitation light can be provided to the tissue through a separate light channel and/or lenses, e.g. provided outside of a camera head.

Figure 1B:
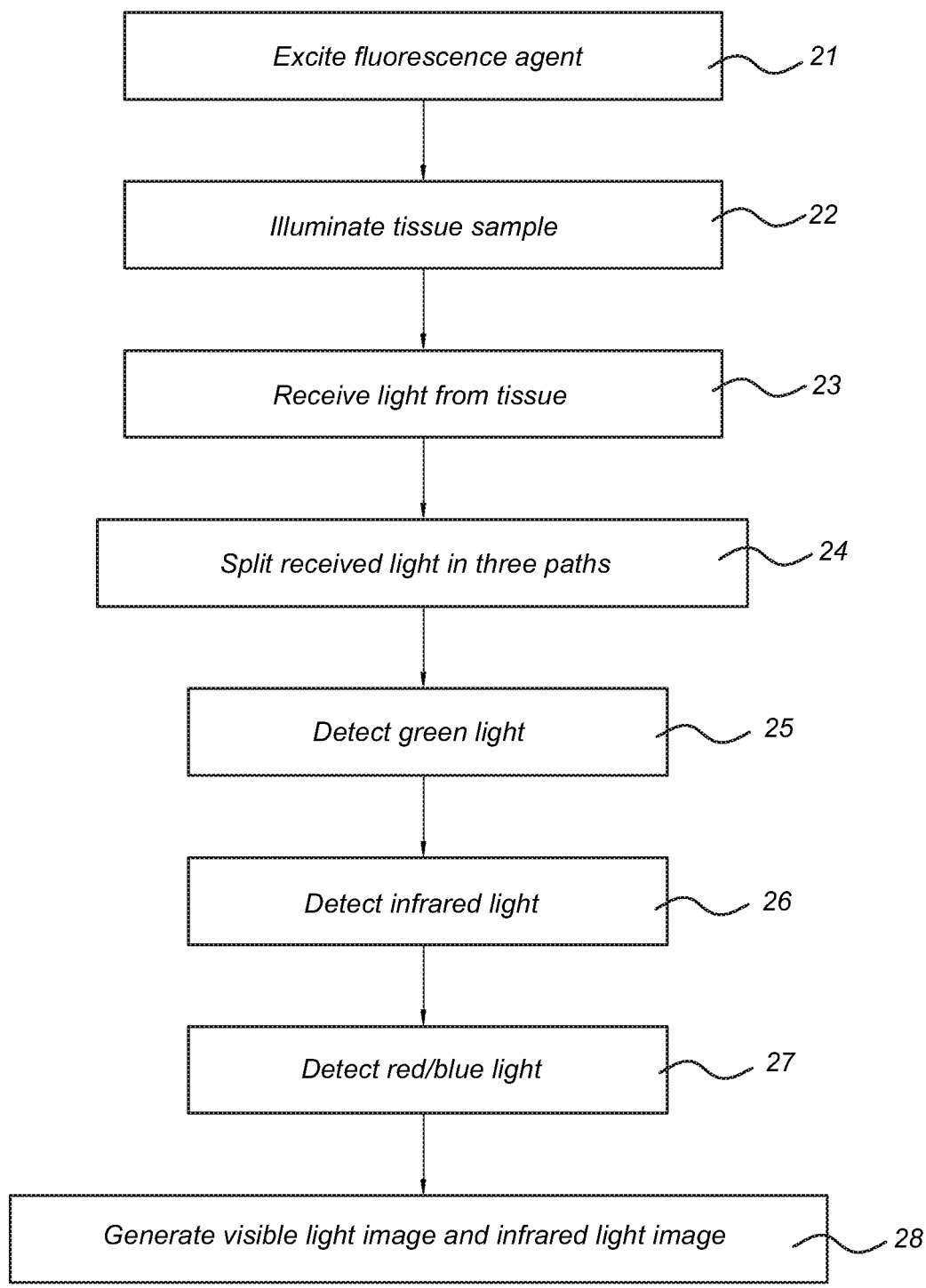
FIG. 1b schematically shows a method according to an embodiment of the invention.

FIG. 1b schematically shows a method for detecting visible and infrared light using a medical imaging system as shown in FIG. 1a. In step 21, a fluorescence agent in a tissue sample is illuminated with excitation light, causing fluorescence light to be emitted by the agent. Meanwhile, in step 22, the tissue sample is also illuminated with visible light. Light from the object image (the tissue sample) is received in step 3, said light comprising visible light and infrared fluorescence light originating from the fluorescence agent. The received light is split into a first, second, and third optical path (step 24), and filtered through a first (green), second (infrared) and third (red/blue) optical filter, respectively. The filtered light is detected by respective sensors (steps 25, 26, 27). In step 28, a visible light image and infrared (fluorescence) image is generated from the detected light. The visible light image may be shown separately from the fluorescence image. It is also possible to show the fluorescence image as an overlay on the visible light image.

Figure 2:
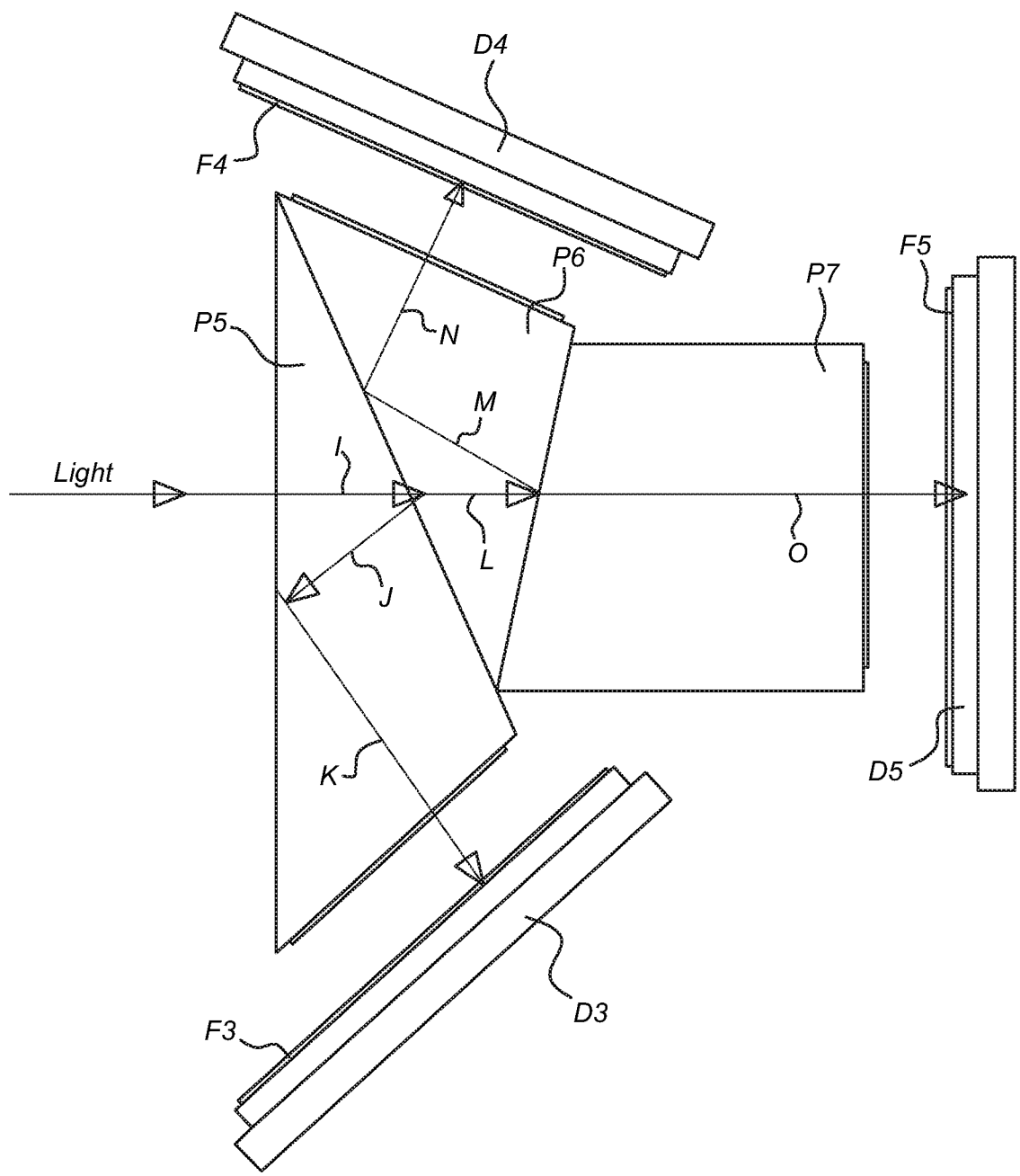
FIG. 2 schematically shows a dichroic prism assembly according to an embodiment of the invention.

FIG. 2 shows a prism assembly comprising prisms P5, P6, and P7 for splitting light in red, green and blue components towards respective sensors D3, D4, and D5. The light enters the prism assembly through the arrow indicated in FIG. 2. Between P5 and P6, an optical coating C1 is placed and between prisms P6 and P7 an optical coating C2 is placed, each optical coating C1 and C2 having a different reflectance and wavelength sensitivity. At C1, the incoming beam I is partially reflected back to the same face of the prism as through which the light entered (beam J). At that same face, the beam, now labelled K, is once again reflected towards filter F3 and sensor D3. The reflection from J to K is an internal reflection. Thus, filter F3 and sensor D3 receive light reflected by coating C1, and in analogue fashion filter F4 and sensor D4 receive light from beam L reflected by coating S2 (beams M and N), and filter F5 and sensor D5 receives light from beam O that has traversed the prism unhindered.

FIG. 3a schematically shows a patterned filter 20 according to the invention, in particular with an array of red and blue filters in an alternating pattern. The pattern 20 consist of groups of 2×2 pixels which are filtered for one particular colour. The groups labelled 21 and 22 are intermixed in a checkboard pattern. Pixels in group 21 have a red filter, and pixels in group 22 have a blue filter. For example the top left group 21 has red pixels R1, R2, R3, R4 in a 2×2 grid and the neighbouring group 22 has blue filtered pixels B1, B2, B3, B4 in a 2×2 grid.

FIG. 3b schematically shows a filter 23 comprising only green filters. For comparison with FIGS. 3a and 3d, the pixels are still shown as divided in 2×2 groups, but in fact there is a single pixel grid with the light received at each pixel being filtered with a green filter. The pixels are therefore labelled in ascending order going from left to right and from top to bottom as G1, G2, G3, etc.

FIG. 3c schematically shows a filter 25 comprising only IR filters. Again, for clarity, the pixels are still shown as divided in 2×2 groups. Now each pixel is filtered with an IR filter. As in FIG. 3b, the pixels are labelled in ascending order going from left to right and from top to bottom as I1, I2, I3, etc.

FIG. 3d schematically shows a patterned filter 27 comprising two different types of IR filters. As in FIG. 3a, the pixels are divided in groups of 2×2 pixels and each group has a specific filter. Groups 28 have a first IR filter and groups 29 have a second IR filter. The pixels in the first groups 28 are labelled I1, I, I3, I4, etc., while the pixels in the second groups 29 are labelled J1, J2, J3, J4. This type of filter can be used for applications where more than one wavelength range in the IR is of interest.

The filters 20 (FIG. 3a, red/blue) and 27 (FIG. 3d, two types of IR) have in common that spatial interpolation will be required to calculate at each pixel position, a red, blue, first IR, and second IR value. The filters 23 (FIG. 3b, green) and 25 (FIG. 3c, IR) do not have this requirement, since each pixel is filtered using the same filter.

The present invention is not limited to the example patterned filters of FIG. 3a-d. What is important is that pattern filter 20 consists of a combination of red and blue filters (no other colours) in a single patterned filter, wherein the red and blue filters are arranged in a structure to allow interpolation of the blue values at pixel locations where red filters are located and interpolation of the red values at pixel locations where blue filters are located. The 2×2 grouping of red and blue filters as shown in FIG. 3a has an additional advantage in that within the group of identical filters, noise cancelation can be performed to reduce single pixel noise before interpolation, increasing image quality. That is, because it can be assumed that pixels in a 2×2 grid receive more or less the same light intensity, it is possible to identify and filter out a values from a malfunctioning pixel.

The grid shown in FIG. 3a, using 2×2 islands of red and blue filtered pixels, is merely an example. For example, it is also possible to alternate red and blue filters in a checkerboard pattern at a pixel-by-pixel basis, as in R-B-R-B-R-B- . . . . It is also possible to have groups of e.g. 1×2 pixels or 2×1 pixels, or any other group size. These considerations do not only apply to the red/blue pattern filter 20 of FIG. 3a, but also, mutatis mutandis, to the first and second IR filter pattern filter 27 of FIG. 3d.

Some example wavelength ranges for filters are now mentioned. A blue filter may filter light in the 400-490 nanometre (nm) range. A red filter may filter 590-660 nm. A green filter may operate in the 490-590 nm range. For infrared, the ranges will depend on the application. Generally speaking, there are ranges of interest between 700 and 800 nm and between 800 and 900 nm.

Turning back to FIGS. 1 and 2, in an embodiment of the invention the filter F3 is a filter 20 (red/blue), F4 is a filter 23 (green), and F5 is a filter 25 (IR). Note that the exact mapping to filters F3, F4, F5 is not important. What is important for any application is which three filters are used simultaneously.

In general, the coatings C1, C2, C3 should match the filters F1, F2, F3. For example, the first coating C1 may transmit visible light while reflecting IR light, so that IR light is guided towards IR filter F3, being an IR filter 25 or 27. The second coating C2 may be transparent for green light while reflecting red and blue light, so that filter F4 should be the red/blue patterned filter 20 and F5 should be the green filter 23. These principles for choosing an appropriate coating can be generally applied to the embodiments disclosed in the description. For brevity, in the following embodiments, no more mention will be made of the used coatings between prisms.

It is an advantageous aspect of the invention that both the green light and the IR light in this case do not require interpolation. The red and blue pixels behind the patterned filter 20 of FIG. 3a do require spatial interpolation. However, the human eye is not as sensitive to details in the red and blue parts of the spectrum as it is to green. This can for example be seen from the equation for calculated luminance (luma, L), which reads:

$$L = 0.2126*R + 0.7152*G + 0.0722*B \tag{1}$$

Luminance can be seen as the grey-scale representation of visible light, and is most important for distinguishing detail.

From this equation it is clear that green light has by far the highest weight. Therefore, it is an advantageous aspect of the present invention that the green light is not interpolated. At the same time, because of the above considerations, it is considered an acceptable trade-off that the red and blue parts of the spectrum are spatially interpolated. The IR signal is again not interpolated.

As was already mentioned, an additional advantage of choosing the 2×2 filter approach is the possibility of image noise reduction. In images produced by standard Bayer filters, the noise in these visible images is apparent by single pixels highlighting red or blue. This is due to the fact that red and blue need higher gains than green (and thus more noise is apparent), but because these pixels (when interpolating) have no direct neighbouring pixels of the same colour, the amount of pixel noise cannot be estimated and therefore not reduced before interpolation. This results in the fact that the interpolation is based on the noise in the pixel and as a result the noise is interpolated as well. It is an advantageous part of the invention when using the 2×2 patterns, that the group of 4 adjacent pixels of the same colour can be used to reduce single pixel image noise with standard available algorithms before interpolation, resulting in a higher quality image.

In a variant of the above, for applications where two different IR wavelength ranges are to be sampled, the pattern filers 20, 23, and 27 (with two different IR filters) can be used for filters F3, F4, F5 in FIGS. 1a and 2. Again, the green light is sampled at full resolution for maximum detail. Red/blue and both IR wavelength ranges are sampled at half resolution, as a trade-off.

Figure 4:
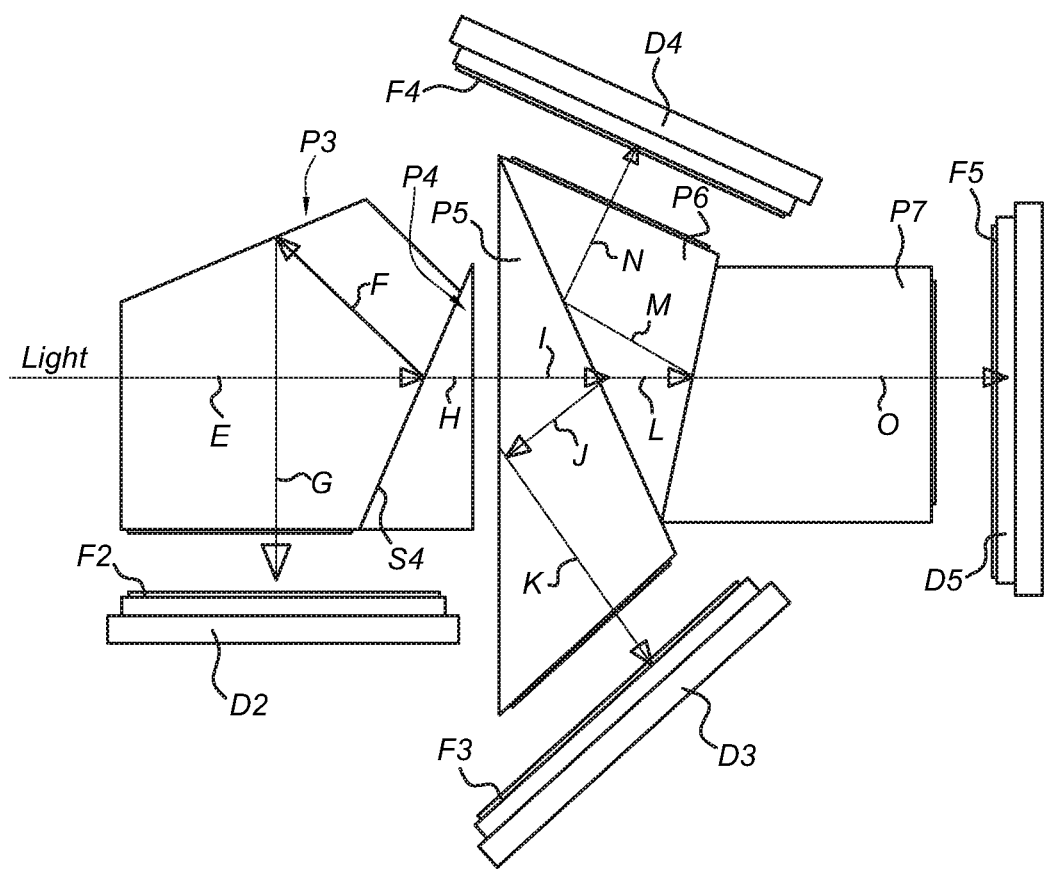
FIG. 4 schematically shows a further dichroic prism assembly according to an embodiment of the invention.
Figure 5:
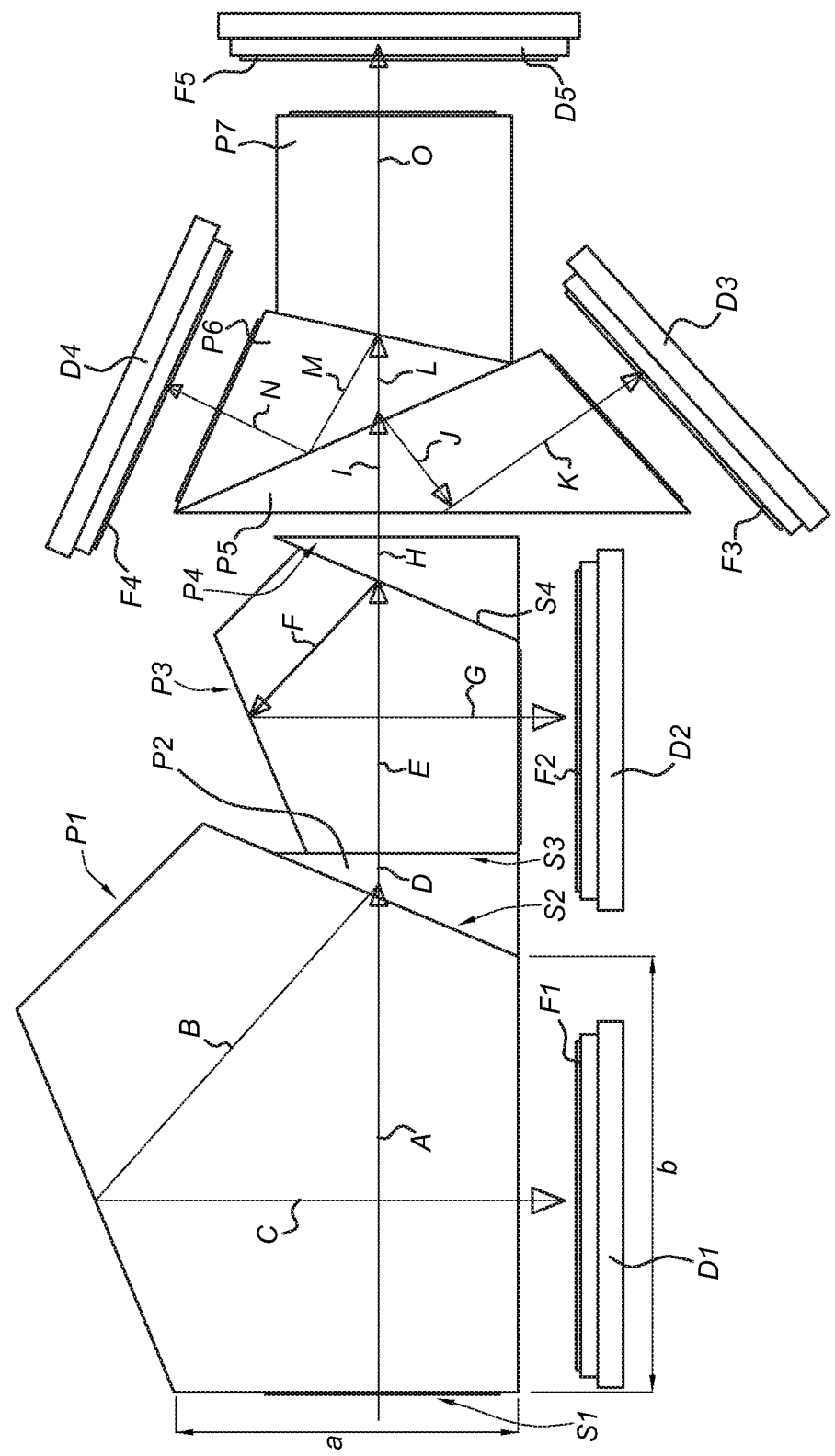
FIG. 5 schematically shows a dichroic prism assembly according to an embodiment of the invention.

FIGS. 4 and 5 schematically show a dichroic prism assembly according to an embodiment of the invention. In FIG. 4, compared to FIG. 5, the first pentagonal prism P1 and the first compensator prism P2 are absent. The resulting dichroic prism assembly of FIG. 3 has four channels, each respective channel formed by a path to one of the sensors D2-D5. The following path lengths are defined for each channel:

Sensor D2 (e.g. near infrared) path: E+F+G
Sensor D3 (e.g. red) path: E+H+I+J+K
Sensor D4 (e.g. blue) path: E+H+I+O
Sensor D5 (e.g. green) path: E+H+I+M+N The path lengths are matched, so that E+F+G=E+H+I+J+K=E+H+I+O=E+H+I+M+N.

The following description of the exemplary embodiment will refer to FIG. 5, with the understanding that the description of prisms P3-P7 is also applicable to the example of FIG. 4.

In an embodiment of the invention, a pentagonal prism P1 is used. In an embodiment, the incoming light beam A is partially reflected on face S2, being one of the two faces not adjoining the entrance face 51. The reflected beam B is then reflected against a first one of the faces adjoining the entrance face. The angle of reflection can be below the critical angle, so that the reflection is not internal (in an embodiment, the adjoining face is coated to avoid leaking of light and reflect the required wavelength of interest). The reflected beam C then crosses itself (beam A) and exits the prism through the second one of the faces adjoining the entrance face, towards sensor D1. A part of the beam A goes through face S2 and enters compensating prism P2.

In an embodiment according the invention, prism P1 does not use internal reflection to reflect the incoming beam towards sensor D1. In an embodiment, two non-internal reflections are used to direct the incoming beam A via beams B and C towards sensor D1. In an embodiment there are no airgaps between prisms P1 and P2. In an embodiment, there are no airgaps between prisms P3 and P4. In an embodiment, there are no airgaps between prisms P2 and P3.

Prism P2 is a compensator prism which can be moved vertically in order to adjust the relative beam distances.

In an embodiment of the invention, from P2 the beam D enters a second pentagonal prism P3. As in prism P1, inward reflection is used to make the beam cross itself. For brevity, the description of the beam will not be repeated, except to state that in prism P3, the beam parts E, F, and G correspond to beam parts A, B, and C in prism P1, respectively.

In an embodiment according the invention, prism P3 also does not use internal reflection to reflect the incoming beam towards sensor D2. In an embodiment, two non-internal reflections are used to direct the incoming beam E via beams F and G towards sensor D2. In an embodiment there are no airgaps between prisms P1, P2, P3, and P4.

After prism P3, there is another compensating prism P4. Finally, beam H enters the dichroic prism assembly comprising prisms P5, P6, and P7, with sensors D3, D4, and D5 respectively. The dichroic prism assembly of P5, P6, and P7 has already been described in reference to FIG. 2. In an embodiment, between prism P4 and prism P5 there is an air gap.

In FIG. 5, the following total path lengths are defined for each endpoint channel (defined in terms of the sensor at the end of the channel):

Sensor D1 (e.g. first near infrared) path: A+B+C
Sensor D2 (e.g. second near infrared) path: A+D+E+F+G
Sensor D3 (e.g. red) path: A+D+E+H+I+J+K
Sensor D4 (e.g. blue) path: A+D+E+H+I+O
Sensor D5 (e.g. green) path: A+D+E+H+I+M+N In an embodiment, the path lengths are matched, so that A+B+C=A+D+E+F+G=A+D+E+H+I+J+K=A+D+E+H+I+O=A+D+E+H+I+M+N. The matching of path lengths can comprise an adjustment for focal plane focus position differences in wavelengths to be detected at the sensors D1-D5. That is, for example the path length towards the sensor for blue (B) light may not be exactly the same as the path length towards the sensor for red (R) light, since the ideal distances for creating a sharp, focused image are somewhat dependent on the wavelength of the light. The prisms can be configured to allow for these dependencies.

The D+H lengths can be adjusted and act as focus compensators due to wavelength shifts.

A larger airgap in path I can be used for additional filters or filled with glass compensator for focus shifts and compensation. An airgap needs to exist in that particular bottom surface of red prism because of the internal reflection in the path from beam J to beam K. A space can be reserved between the prism output faces and each of the sensors D1-5 to provide an additional filter, or should be filled up with glass compensators accordingly.

An advantage of the fact that P1 and P3 use essentially the same reflection paths, is that this way the optical assembly can have sensors mostly on one side (D1, D2, D3 are all on one side), still use an even amount of direction change so all sensors see the same image and no mirror effects need to be compensated for.

Normally optical prisms are designed as in the case of the three channel blue green and red channels, and that way the path length would require a very long and particularly wide prism, which would result in a large module which is less suitable for use in an endoscope or laparoscope or handheld imaging system. Furthermore the two channels (sensors D1 and D2) would need to be opposite of each other which also makes the electronics more cumbersome as the large distance between the 2 sensors. In the embodiment of FIG. 5, the two sensors D1 and D2 can be on the same side as prisms P1 and P3.

According an embodiment of the invention, the first two prisms P1, P3 have a pentagonal shape where at least five corners are used and all corners have an inside angle >=90 degree.

Each of these prisms has an additional compensator prism P2, P4 to create a flat exit surface pane for the light and at the same time have a path length compensation function to be able to match the path lengths of all sensors.

In an embodiment according the invention, the dimensions are given as follows. Total height of the module is ≤30 mm or smaller for a 5-channel configuration including the sensors. The maximum width ≤15 mm. The maximum length ≤45 mm.

In an embodiment according the invention, a system using a dichroic prism assembly has a capability to create image resolutions in full colour without artefacts at 3840×2160 @ 12 bit per colour at 60 Fps without using infrared frame insertion. Infrared frames are available as well at these same resolution @ 12 bit.

Another advantage of the current invention is that because all surfaces that connect the paths to D1 and D2 are flat. Accordingly the modules (P1, P2, P3, P4) can be easily aligned which makes automatic assembly easy. These modules can be prepared individually and afterwards bonded together with a simple robotic or manual tool.

The second prism P3 (for the D2 path) can be smaller than the prism P1 (for the D1 path), because path length A is already compensated for. In order to shape the first prism for the path to D1 with a slightly longer length (A) a perfect match can be created between the total internal path to D1 and compensate as much as possible for the total length of the path to D2.

The pentagonal prisms are usually not regular. For example, length a (influencing the length of beams B and C) of the P1 cross section may be smaller than length b (influencing the length of beams A and B).

The above described dichroic prism assemblies of FIG. 4 (with four sensors F2-F5) and FIG. 5 (with five sensors F1-F5) make further exemplary embodiments possible, which are below presented schematically:
- an application using two different IR wavelength ranges: the four-channel dichroic prism assembly of FIG. 4, with for each respective channel, pattern filters 20 (red/blue), 23 (green), 25 (first IR), and 25 (second IR wavelength range);
- an application using three different IR wavelength ranges: the four-channel dichroic prism assembly of FIG. 4, with for each respective channel, pattern filters 20 (red/blue), 23 (green), 25 (first IR), and 27 (second and third IR wavelength range);
- an application using four different IR wavelength ranges: the four-channel dichroic prism assembly of FIG. 4, with for each respective channel, pattern filters 20 (red/blue), 23 (green), 27 (first and second IR), and 27 (third and fourth IR wavelength range);
- an application using three different IR wavelength ranges: the five-channel dichroic prism assembly of FIG. 5, with for each respective channel, pattern filters 20 (red/blue), 23 (green), 25 (first IR), another 25 (second IR wavelength range), and yet another 25 (third IR wavelength range);

Still more combinations can be made using the dichroic prism assemblies of FIGS. 2, 4, and 5 and the pattern filters 20, 23, 25, 27.

As was already mentioned, the present invention is not limited to the example pattern filters of FIG. 3a-d. The grid shown in FIG. 3a, using 2×2 islands of red and blue filtered pixels, is merely an example.

Figure 6A:
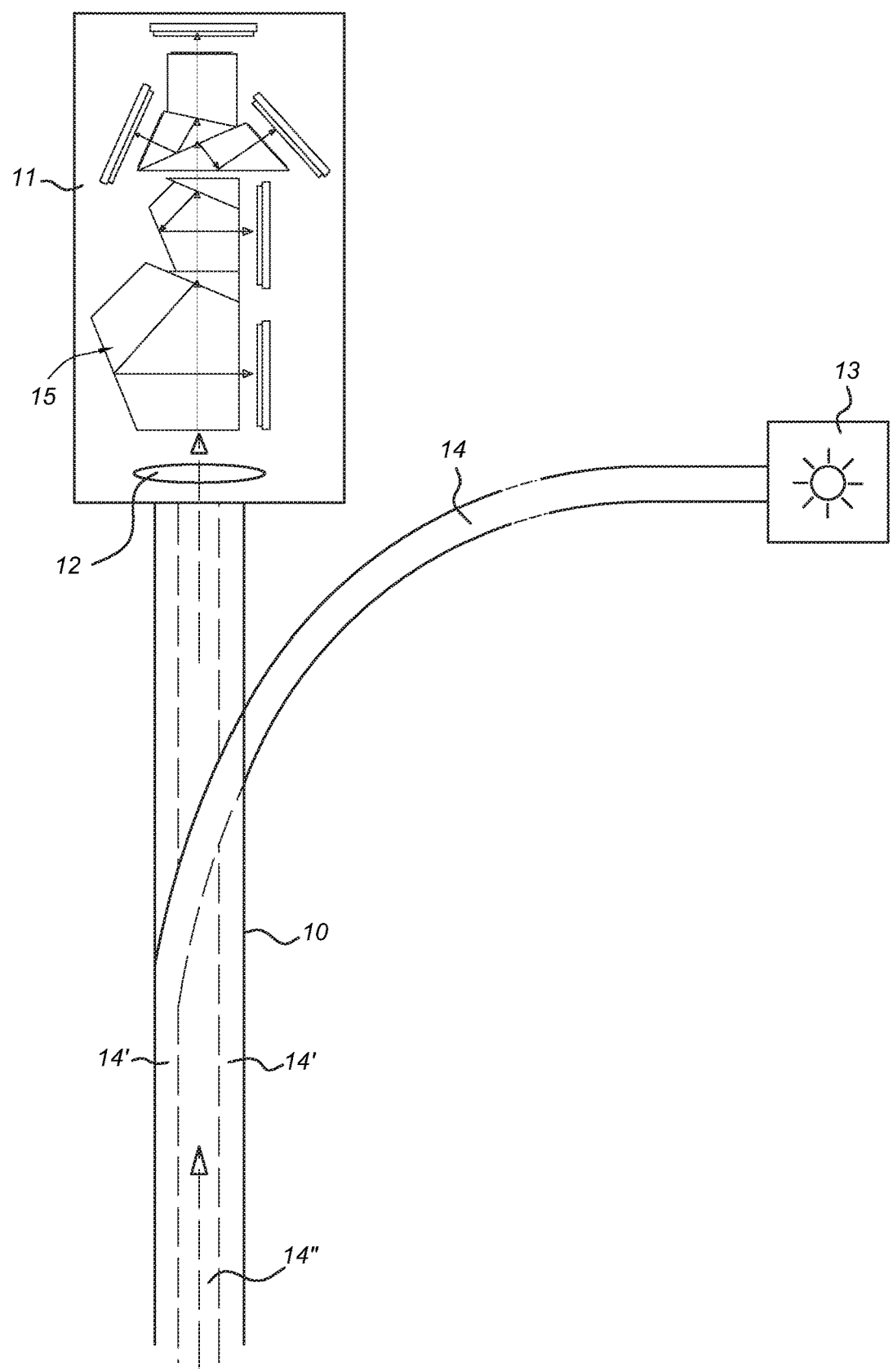
FIGS. 6a-c schematically show an endoscope and/or laparoscope and cabling according to an embodiment of the invention.

FIG. 6a schematically shows an endoscope 10 or laparoscope 10, according to an embodiment of the invention. For the purposes of this invention, the differences between laparoscopes and endoscopes are relatively small, so where the description mentions an endoscope, a laparoscope configuration is usually also possible. The endoscope/laparoscope 10 comprises camera module 11 including a dichroic prism assembly 15 such as shown in FIG. 2, 4 or 5. The camera module 11 may also include an additional lens 12 for focusing incident light onto the entrance face of the dichroic prism assembly 15. This last lens 12 may also be integrated in the last part of the endoscope part to match the prism back focal length. An optical fiber 14 connected to a light source 13 couples light into the endoscope 10. Inside the endoscope, optical fiber 14 splits off into several fibers 14'.

Inside the laparoscope a lens system is created consisting of lens elements and/or relay rod lenses (similar as in standard laparoscopes) or, in an endoscope configuration, a fiber bundle can be used like in a standard flexible endoscope. Furthermore a processing unit (not shown) may be placed in the camera module 11 for high speed image processing and image cleanup to optionally reduce data such that it does not have to be transmitted.

In another embodiment of the invention, the processing unit is placed further away from the imaging system and optical elements. A key issue with specifically endoscopy systems, but also open configurations, is the cabling which provides the electronic signals of the systems to be transferred between the processing unit and the image sensors placed on the prism elements, and the cables that provide the lighting to the object that is imaged. Most configurations have 2 cabling systems based on Low Voltage Differential Signals (LVDS). The data transfer speed of these cables however is mostly limited to the length of the cable. The optical configuration proposed in this invention means that more data needs to be transferred at a higher bitrate than usual in endoscopic medical imaging systems. Usability and size are largely hindered by the fact that two cables are required (one for light and one electrical for the image and control signals). Simply adding more cable pairs is the standard solution, but the downside of this is that the minimal required thickness of the cables is limiting the flexibility and agility of the camera head. Furthermore the cables will become thicker in diameter and heavier and more electronics is required inside the camera head, which makes the camera head larger and heavier.

Figure 6B:
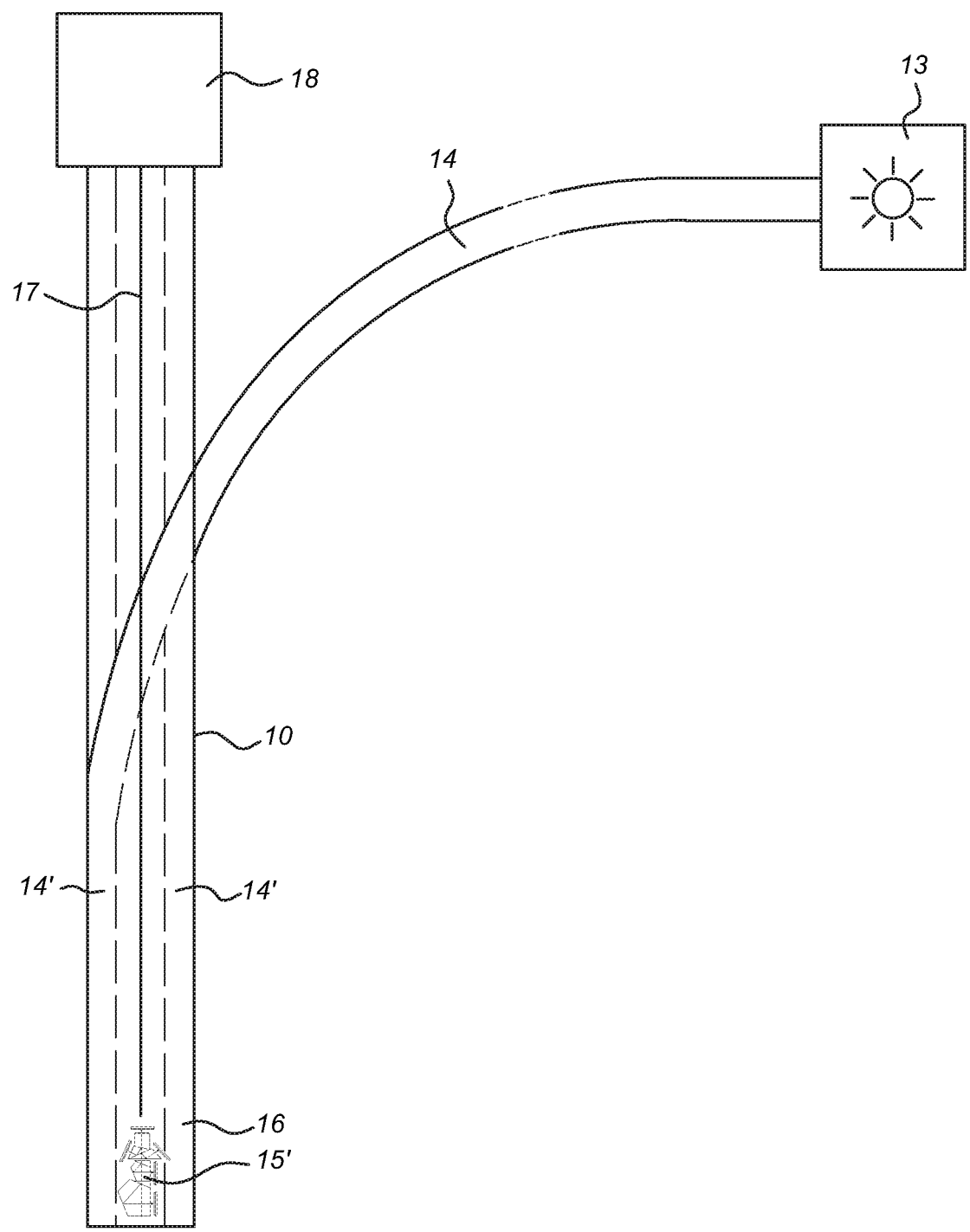

FIG. 6b shows an embodiment where the dichroic prism assembly 15' (for example the assembly shown in FIG. 4 or 5) and the lens 12' are located in the tip of endoscope 10. In this embodiment, there is no need to transport light from the tip to the camera module. However, it is necessary now to transport the signal from the sensors D1-D5 to the module 18 housing the processing unit. The rod relaying lenses normally placed in the tube of the laparoscope, or the fibers in case of an endoscope are no longer required, and only a simple lens system 12' needs to be placed in front of the prism assembly.

Figure 6C:
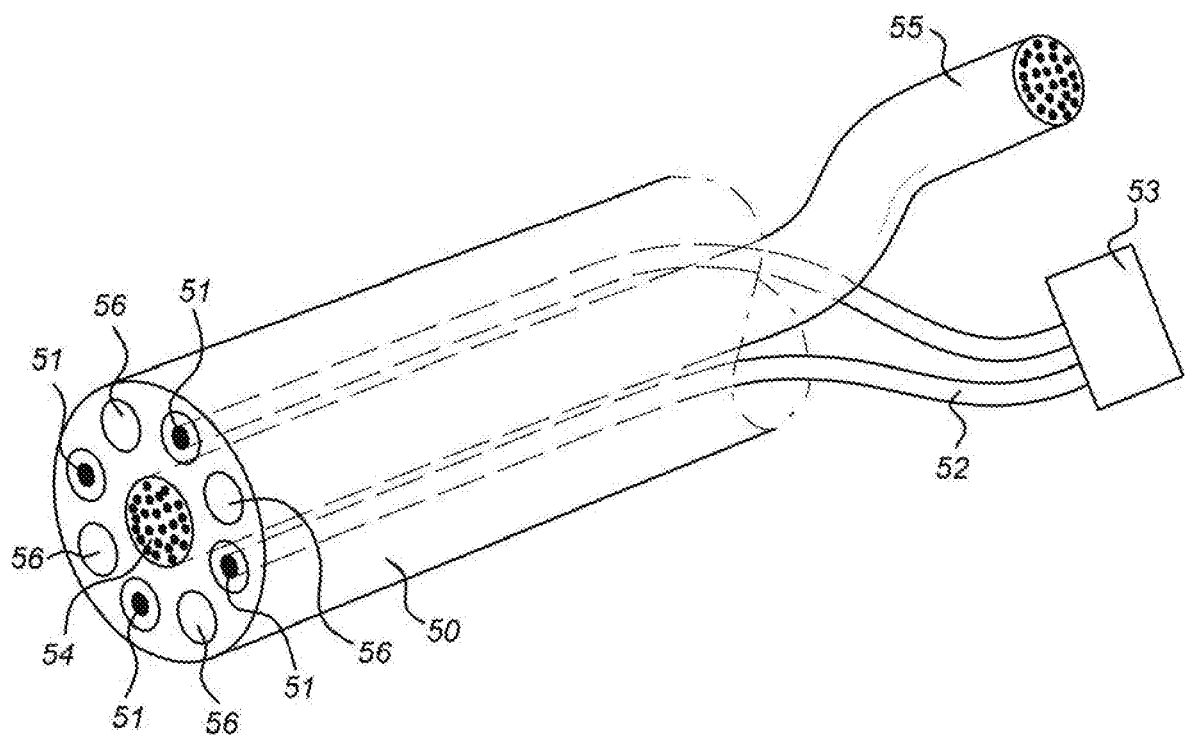

In any of these embodiments, it is possible to include four small diameter coax cables 51 and place these around/integrate these with the fiber optic cable 54. The cable is then fused, together with optional filler cables 56 to improve stability, as an integrated part and a single cable, which is directly coupled between camera and control system with light engine. Such an arrangement is shown in FIG. 6c, where central core fiber 54 can carry light from the light engine to the tip of the endoscope, and the diameter coax cables 51 can carry the signal from detectors D1-D5 located in the tip to the processing unit in housing 53. Depending on the amount of data to be transferred and the required length of the coax cables 51, a suitable number of coax cables can be selected, e.g. one, two, three, four, or more.

Figure 7A:
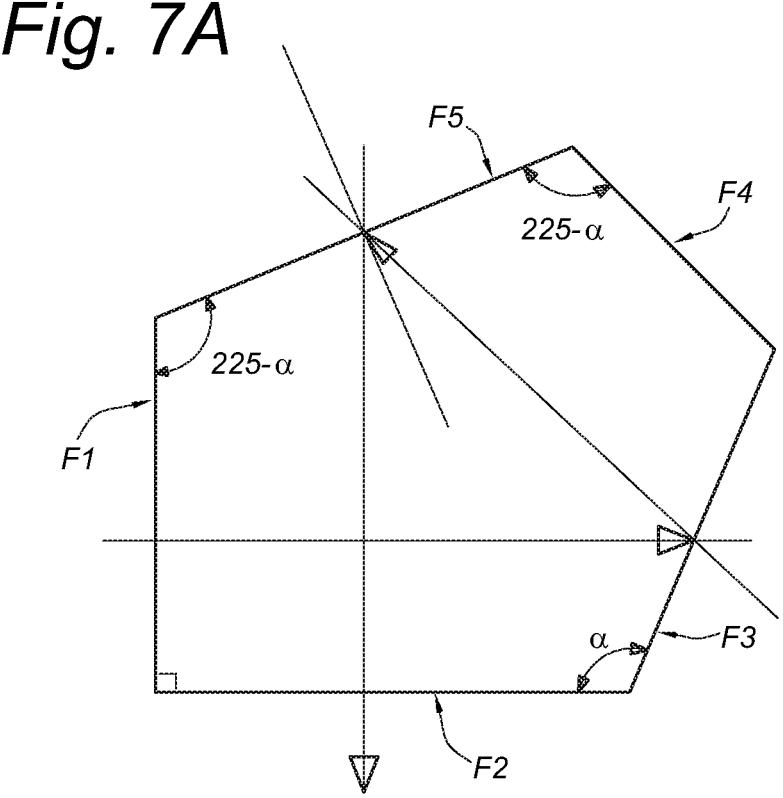
FIGS. 7a-b shows an exemplary pentagonal prism for use in an dichroic prism assembly according to an embodiment of the invention.

FIG. 7a shows a cross section of an exemplary pentagonal prism for use in a dichroic prism assembly according to an embodiment of the invention using the assembly of FIG. 4 or 5.

In an embodiment, the prism P1 or P3 has corners which are designed so that an incoming beam which enters the entrance face in a direction parallel to a normal of said entrance face is reflected twice inside the prism and exits the prism through an exit face parallel to a normal of said exit face, wherein the normal of the entrance face and the normal of the exit face are perpendicular to each other.

A skilled person can design such a prism. In the example of FIG. 7a, one of the five angles is a right angle (between faces F1 and F2), two angles have a first value $\alpha \geq 90$ degrees (between faces F2 and F3 and F3 and F4) and two angles have a second value $225-\alpha$ degrees (between faces F1 and F5 and F5 and F4), making a total inside angle of 540 degrees for a pentagonal prism. As can be easily verified, the pentagonal prism as shown in FIG. 7a will inwardly reflect an incoming horizontal beam, incoming through face F1 in parallel with the normal of face F1, using two reflections against faces F3 and F5, so that it exits the prism in a vertical direction through face F2, in parallel with the normal of face F2. In the first reflection, at face F3, the beams will make an angle with the normal of the face of reflection of $\alpha-90$ degrees. In the second reflection, at face F5, the angle with the normal of the face of reflection is $135-\alpha$. In this example, the angle $\alpha$ should have a value $90<\alpha<135$.

In a specific embodiment, the value of a is 112.5 degrees, so that the pentagonal prism has one right angle and four angles of 112.5 degrees.

Figure 7B:
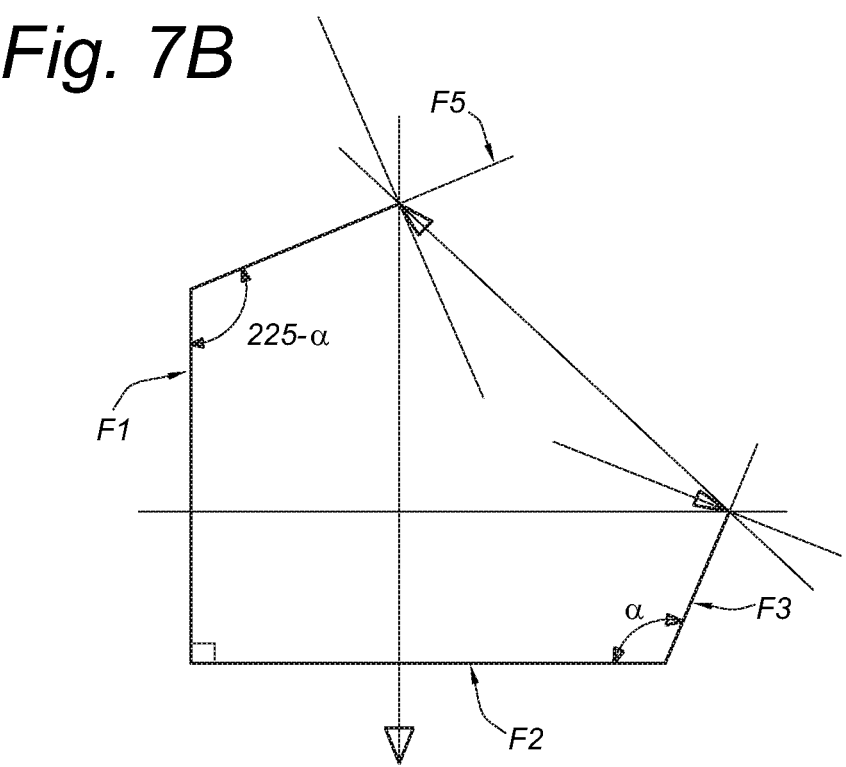

FIG. 7b shows a reduced part of the prism of FIG. 7a. As can be seen from the construction of the lines, it is sufficient if one angle in the prism is 90 degrees (between F1 and F2), an angle adjoining the 90 degrees angle is a, and the other angle (between F1 and F5) adjoining the 90 degrees angle is 225-a. The angles between F3 and F4 and F4 and F5 can in fact be freely chosen.

The skilled person will also be able to design prisms in which the incoming and outgoing beams are not at right angles to each other. However, there are practical advantages to designs, such as the embodiment of FIG. 7b, wherein the incoming and outgoing chief ray beam are at a right angle to each other, as additional angles of light are coming from the lens system.

A pentagonal prism shape is a logical and practical choice for the prisms P1 and P3. However, as is clear from FIG. 7b, in order to create the conditions for the required reflections, in fact many different types of prism shape will serve. The invention is therefore not limited to the use of pentagonal prisms.

In the foregoing description of the figures, the invention has been described with reference to specific embodiments thereof. It will, however, be evident that various modifications and changes may be made thereto without departing from the scope of the invention as summarized in the attached claims.

In addition, many modifications may be made to adapt a particular situation or material to the teachings of the invention without departing from the essential scope thereof. Therefore, it is intended that the invention not be limited to the particular embodiments disclosed, but that the invention will include all embodiments falling within the scope of the appended claims.

In particular, combinations of specific features of various aspects of the invention may be made. An aspect of the invention may be further advantageously enhanced by adding a feature that was described in relation to another aspect of the invention.

It is to be understood that the invention is limited by the annexed claims and its technical equivalents only. In this document and in its claims, the verb "to comprise" and its conjugations are used in their non-limiting sense to mean that items following the word are included, without excluding items not specifically mentioned. In addition, reference to an element by the indefinite article "a" or "an" does not exclude the possibility that more than one of the element is present, unless the context clearly requires that there be one and only one of the elements. The indefinite article "a" or "an" thus usually means "at least one".

The invention claimed is:

1. A method for detecting visible and infrared light using a medical imaging system, said medical imaging system comprising a dichroic prism assembly and a camera module configured to receive visible light and infrared light from an object image, the method comprising:
    exciting a fluorescence agent in a tissue sample with excitation light;
    illuminating the tissue sample with visible light;
    receiving light from the object image through an entrance face of the dichroic prism assembly, said light comprising visible light and one or more infrared fluorescence light originating from the fluorescence agent;
    splitting the received light into a first, second, and third optical path;
    filtering the received light in the first, second, and third optical path through a first, second and third optical filter, respectively;
    detecting the filtered light in the first, second, and third optical path with a first, second and third sensor, respectively wherein the first, second, and third filters, in any order, are a green filter, an infrared filter, and a red/blue patterned filter comprising red and blue filters in alternating pattern so that half of the light received by the red/blue patterned filter goes through a blue filter and half of the light received by the red/blue patterned filter goes through a red filter,
    wherein the dichroic prism assembly comprises at least a first, second, and third prism, each prism having a respective first, second, and third exit face,
    wherein:
    the first exit face is provided with the first sensor,
    the second exit face is provided with the second sensor, and
    the third exit face is provided with the third sensor, and
    wherein the dichroic prism assembly comprises a fourth prism, said fourth prism having a cross section with at least five corners, each corner having an inside angle of at least 90 degrees, the fourth prism providing a fourth optical path with a fourth filter and having a fourth exit face provided with a fourth light sensor, wherein the fourth filter is a second infrared filter.

2. The method according to claim 1, wherein the red/blue patterned filter comprises groups of a plurality of pixels, each group having a filter for either red or blue light.

3. The method according to claim 2, wherein the groups having different filters are arranged in a checkerboard pattern.

4. The method according to claim 1, wherein the infrared filter is transparent for light in an infrared wavelength range, said range starting above 700 nm and ending below 800 nm or starting above 800 nm and ending below 900 nm.

5. The method according to claim 1, wherein the infrared filter comprises groups of one or more pixels, each group having a filter for either a first or second infrared wavelength range, wherein the groups having the first or second infrared wavelength range are arranged in an alternating pattern, such as a checkerboard pattern.

6. The method according to claim 5, wherein the first wavelength range starts above 700 nm and ends below 800 nm and the second wavelength range starts above 800 nm and ends below 900 nm.

7. The method according to claim 1, further comprising:
in addition to the splitting of the received light into a first, second, and third optical path, splitting the received light into a fourth optical path, and filtering the received light in the fourth optical path through a fourth optical filter, wherein the fourth optical filter is a second infrared filter.

8. A medical imaging system for detecting visible and infrared light, said medical imaging system comprising
an input for visible light for illuminating a tissue;
an input for excitation light for exciting a fluorescence agent in the tissue;
a camera module configured to receive visible light and infrared light from an object image in the tissue, the camera module comprising at least a first, second, and third optical path for directing light from the object image to a first, second, and third sensor respectively, and
a dichroic prism assembly configured to receive the light from the object image through an entrance face of the dichroic prism assembly, comprising at least a first, second, and third prism, each prism having a respective first, second, and third exit face, wherein:
the first optical path is provided with a first filter,
the second optical path is provided with a second filter, and
the third optical path is provided with a third filter,
wherein the first, second, and third filters, in any order, are a green filter, an infrared filter, and a red/blue patterned filter comprising red and blue filters in alternating pattern so that half of the light received by the red/blue patterned filter goes through a blue filter and half of the light received by the red/blue patterned filter goes through a red filter,
wherein:
the first exit face is provided with the first sensor,
the second exit face is provided with the second sensor, and
the third exit face is provided with the third sensor, and
wherein the dichroic prism assembly comprises a fourth prism, said fourth prism having a cross section with at least five corners, each corner having an inside angle of at least 90 degrees, the fourth prism providing a fourth optical path with a fourth filter and having a fourth exit face provided with a fourth light sensor, wherein the fourth filter is a second infrared filter.

9. The medical imaging system according to claim 8, wherein the red/blue patterned filter comprises groups of a plurality of pixels, each group having a filter for either red or blue light.

10. The medical imaging system according to claim 9, wherein the groups having different filters are arranged in a checkerboard pattern.

11. The medical imaging system according to claim 8, wherein the infrared filter is transparent for light in an infrared wavelength range, said range starting above 700 nm and ending below 800 nm or starting above 800 nm and ending below 900 nm.

12. The medical imaging system according to claim 8, wherein the infrared filter comprises groups of one or more pixels, each group having a filter for either a first or second infrared wavelength range, wherein the groups having the first or second infrared wavelength range are arranged in an alternating pattern, such as a checkerboard pattern.

13. The medical imaging system according to claim 12, wherein the first wavelength range starts above 700 nm and ends below 800 nm and the second wavelength range starts above 800 nm and ends below 900 nm.

14. The medical imaging system according to claim 8, comprising a fifth prism, said fifth prism having a cross section with at least five corners, each corner having an inside angle of at least 90 degrees, the fifth prism providing a fifth optical path with a fifth filter and having a fifth exit face provided with a fifth light sensor, wherein the fifth filter is a third infrared filter.

15. Endoscope or laparoscope or open lens system comprising at least one medical imaging system according to claim 8.

16. The endoscope or the laparoscope or the open lens system according to claim 15, further comprising a lens for focusing light onto the camera module.

17. The endoscope or the laparoscope or the open lens system according to claim 15, using an integrated cable comprising an optical fiber core for providing light from a light engine onto a surgical field to illuminate, the optical fiber core surrounded by a plurality of coax cables for transporting sensor data.

18. The endoscope or the laparoscope or the open lens system according to claim 15, wherein a frame acquisition frequency is at least 60 frames per second and a sampling rate is at least 8 bits per pixel.

* * * * *